United States Patent
LeBoeuf

(10) Patent No.: US 9,427,191 B2
(45) Date of Patent: Aug. 30, 2016

(54) APPARATUS AND METHODS FOR ESTIMATING TIME-STATE PHYSIOLOGICAL PARAMETERS

(75) Inventor: Steven Francis LeBoeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 256 days.

(21) Appl. No.: 14/116,641

(22) PCT Filed: Jul. 12, 2012

(86) PCT No.: PCT/US2012/046446
§ 371 (c)(1),
(2), (4) Date: Nov. 8, 2013

(87) PCT Pub. No.: WO2013/016007
PCT Pub. Date: Jan. 31, 2013

(65) Prior Publication Data
US 2014/0128690 A1    May 8, 2014

(51) Int. Cl.
| A61B 5/02 | (2006.01) |
|---|---|
| A61B 5/00 | (2006.01) |
| A61B 5/0205 | (2006.01) |
| A61B 5/1455 | (2006.01) |
| A61B 5/021 | (2006.01) |
| A61B 5/024 | (2006.01) |
| A61B 5/08 | (2006.01) |

(52) U.S. Cl.
CPC ......... *A61B 5/4866* (2013.01); *A61B 5/02055* (2013.01); *A61B 5/14551* (2013.01); *A61B 5/4857* (2013.01); *A61B 5/021* (2013.01); *A61B 5/02405* (2013.01); *A61B 5/0816* (2013.01); *A61B 2560/0242* (2013.01)

(58) Field of Classification Search
CPC ............ A61B 5/4866; A61B 5/14551; A61B 5/4857; A61B 5/02055; A61B 5/021; A61B 2560/0242; A61B 5/02405; A61B 5/0816
See application file for complete search history.

(56) References Cited

U.S. PATENT DOCUMENTS

| 3,595,219 A | 7/1971 | Friedlander et al. |
|---|---|---|
| 4,240,882 A | 12/1980 | Ang et al. |

(Continued)

FOREIGN PATENT DOCUMENTS

| DE | 3910749 A1 | 10/1990 |
|---|---|---|
| EP | 1 480 278 A2 | 11/2004 |

(Continued)

OTHER PUBLICATIONS

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

(Continued)

*Primary Examiner* — Rex R Holmes
(74) *Attorney, Agent, or Firm* — Myers Bigel & Sibley, P.A.

(57) ABSTRACT

A method of determining a value of a physiological parameter for a subject at a selected state includes obtaining, via a device attached to the subject, a value of the physiological parameter of the subject at a particular time-of-day, and applying a time-dependent relationship function to the obtained physiological parameter value via a processor to determine a value of the physiological parameter at the selected state.

22 Claims, 11 Drawing Sheets

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,882,492 A | 11/1989 | Schlager |
| 4,896,676 A | 1/1990 | Sasaki |
| 4,928,704 A | 5/1990 | Hardt |
| 4,957,109 A | 9/1990 | Groeger et al. |
| 5,002,060 A | 3/1991 | Nedivi |
| 5,022,970 A | 6/1991 | Cook et al. |
| 5,079,421 A | 1/1992 | Knudson et al. |
| 5,086,229 A | 2/1992 | Rosenthal et al. |
| 5,143,078 A | 9/1992 | Mather et al. |
| 5,226,417 A | 7/1993 | Swedlow et al. |
| 5,348,002 A | 9/1994 | Caro |
| 5,377,100 A | 12/1994 | Pope et al. |
| 5,482,036 A | 1/1996 | Diab et al. |
| 5,492,129 A | 2/1996 | Greenberger |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,807,114 A | 9/1998 | Hodges et al. |
| 5,807,267 A | 9/1998 | Bryars et al. |
| 5,853,005 A | 12/1998 | Scanlon |
| 5,904,654 A | 5/1999 | Wohltmann et al. |
| 5,938,593 A | 8/1999 | Ouellette |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,013,007 A | 1/2000 | Root et al. |
| 6,023,541 A | 2/2000 | Merchant et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,209,775 B2 | 4/2007 | Bae et al. |
| 7,252,639 B2 | 8/2007 | Kimura et al. |
| 7,263,396 B2 | 8/2007 | Chen et al. |
| 7,336,982 B2 | 2/2008 | Yoo et al. |
| 7,341,559 B2 | 3/2008 | Schulz et al. |
| 7,376,451 B2 | 5/2008 | Mahony et al. |
| 7,470,234 B1 | 12/2008 | Elhag et al. |
| 7,483,730 B2 | 1/2009 | Diab et al. |
| 7,486,988 B2 | 2/2009 | Goodall et al. |
| 7,519,327 B2 | 4/2009 | White |
| 7,583,994 B2 | 9/2009 | Scholz |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 8,050,728 B2 | 11/2011 | Al-Ali et al. |
| 8,055,319 B2 | 11/2011 | Oh et al. |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,172,459 B2 | 5/2012 | Abreu |
| 8,175,670 B2 | 5/2012 | Baker, Jr. et al. |
| 8,251,903 B2 | 8/2012 | LeBoeuf et al. |
| 8,255,027 B2 | 8/2012 | Al-Ali et al. |
| 8,328,420 B2 | 12/2012 | Abreu |
| 8,416,959 B2 | 4/2013 | Lott et al. |
| 8,491,492 B2 * | 7/2013 | Shinar .................. A61B 5/0205 600/16 |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,730,048 B2 | 5/2014 | Shen et al. |
| 9,005,129 B2 | 4/2015 | Venkatraman et al. |
| 2001/0049471 A1 | 12/2001 | Suzuki et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |

(56) References Cited

U.S. PATENT DOCUMENTS

| | | |
|---|---|---|
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert |
| 2005/0058456 A1 | 3/2005 | Yoo |
| 2005/0059870 A1 | 3/2005 | Aceti |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0240087 A1 | 10/2005 | Keenan et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0122520 A1 | 6/2006 | Banet et al. |
| 2006/0123885 A1 | 6/2006 | Yates et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0036383 A1 | 2/2007 | Romero |
| 2007/0060800 A1 | 3/2007 | Drinan et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0106167 A1 | 5/2007 | Kinast |
| 2007/0112598 A1 | 5/2007 | Heckerman et al. |
| 2007/0116314 A1 | 5/2007 | Grilliot et al. |
| 2007/0118054 A1 | 5/2007 | Pinhas et al. |
| 2007/0165872 A1 | 7/2007 | Bridger et al. |
| 2007/0167850 A1 | 7/2007 | Russell et al. |
| 2007/0197881 A1 | 8/2007 | Wolf et al. |
| 2007/0213020 A1 | 9/2007 | Novac |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2008/0004536 A1 | 1/2008 | Baxi et al. |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0141301 A1 | 6/2008 | Azzaro et al. |
| 2008/0146890 A1 | 6/2008 | LeBoeuf et al. |
| 2008/0146892 A1 | 6/2008 | LeBoeuf et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0249594 A1 | 10/2008 | Dietrich |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0030350 A1 | 1/2009 | Yang et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0112071 A1 | 4/2009 | LeBoeuf et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |

(56) References Cited

U.S. PATENT DOCUMENTS

| | | | |
|---|---|---|---|
| 2010/0172522 | A1 | 7/2010 | Mooring et al. |
| 2010/0179389 | A1 | 7/2010 | Moroney et al. |
| 2010/0185105 | A1 | 7/2010 | Baldinger |
| 2010/0217099 | A1* | 8/2010 | LeBoeuf .................. A61B 5/00 600/301 |
| 2010/0217102 | A1 | 8/2010 | LeBoeuf et al. |
| 2010/0217103 | A1 | 8/2010 | Abdul-Hafiz et al. |
| 2010/0222655 | A1 | 9/2010 | Starr et al. |
| 2010/0228315 | A1 | 9/2010 | Nielsen |
| 2010/0234714 | A1 | 9/2010 | Mercier et al. |
| 2010/0268056 | A1 | 10/2010 | Picard et al. |
| 2010/0274100 | A1 | 10/2010 | Behar et al. |
| 2010/0274109 | A1 | 10/2010 | Hu et al. |
| 2010/0292589 | A1 | 11/2010 | Goodman |
| 2010/0298653 | A1 | 11/2010 | McCombie et al. |
| 2011/0028810 | A1 | 2/2011 | Van Slyke et al. |
| 2011/0028813 | A1 | 2/2011 | Watson et al. |
| 2011/0081037 | A1 | 4/2011 | Oh et al. |
| 2011/0105869 | A1 | 5/2011 | Wilson et al. |
| 2011/0112382 | A1 | 5/2011 | Li et al. |
| 2011/0130638 | A1 | 6/2011 | Raridan, Jr. |
| 2011/0142371 | A1 | 6/2011 | King et al. |
| 2011/0288379 | A1 | 11/2011 | Wu |
| 2012/0030547 | A1 | 2/2012 | Raptis et al. |
| 2012/0095303 | A1 | 4/2012 | He |
| 2012/0156933 | A1 | 6/2012 | Kreger et al. |
| 2012/0179011 | A1 | 7/2012 | Moon et al. |
| 2012/0197093 | A1 | 8/2012 | LeBoeuf et al. |
| 2012/0277548 | A1 | 11/2012 | Burton |
| 2013/0053661 | A1 | 2/2013 | Alberth et al. |
| 2013/0072765 | A1 | 3/2013 | Kahn et al. |
| 2013/0131519 | A1 | 5/2013 | LeBoeuf et al. |
| 2013/0245387 | A1 | 9/2013 | Patel |
| 2013/0336495 | A1 | 12/2013 | Burgett et al. |
| 2014/0051940 | A1 | 2/2014 | Messerschmidt |
| 2014/0052567 | A1 | 2/2014 | Bhardwaj et al. |
| 2014/0073486 | A1 | 3/2014 | Ahmed et al. |
| 2014/0100432 | A1 | 4/2014 | Golda et al. |
| 2014/0127996 | A1 | 5/2014 | Park et al. |
| 2014/0219467 | A1 | 8/2014 | Kurtz |
| 2014/0236531 | A1 | 8/2014 | Carter |
| 2014/0275852 | A1 | 9/2014 | Hong et al. |
| 2014/0323880 | A1 | 10/2014 | Ahmed et al. |
| 2014/0378844 | A1 | 12/2014 | Fei |

FOREIGN PATENT DOCUMENTS

| | | |
|---|---|---|
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 2003-159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/47108 A1 | 8/2000 |
| WO | WO 01/08552 A1 | 2/2001 |
| WO | WO 02/17782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/053146 A1 | 5/2007 |
| WO | WO 2008141306 A2 | 11/2008 |
| WO | WO 2013/038296 A1 | 3/2013 |
| WO | WO 2014/092932 A1 | 6/2014 |

OTHER PUBLICATIONS

European Search Report, EP Application No. 13863449.8, Oct. 19, 2015, 3 pages.

European Search Report, EP Application No. 14743615.8, Oct. 12, 2015, 3 pages.

European Search Report, EP Application No. 14743839.4, Oct. 12, 2015, 3 pages.

Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.

International Preliminary Report on Patentability, PCT/US2014/012940, Jun. 17, 2015, 23 pages.

International Search Report and Written Opinion of the International Searching Authority, corresponding to International Patent Application No. PCT/US2014/012940, Date of Mailing: Oct. 16, 2014, 13 pages.

International Search Report corresponding to International Patent Application No. PCT/US2014/012909, Date of Mailing: May 13, 2014, 3 pages.

Notification Concerning Transmittal of International Preliminary Report on Patentability, PCT/US2014/012909, Jul. 28, 2015.

Notification of Transmittal of the International Search Report and the Written Opinion of the International Searching Authority, or the Declaration, PCT/US2015/014562, Oct. 28, 2015.

Notification of Transmittal of the International Search Report and the Written Opinion of the International Searching Authority, or the Declaration, PCT/US2015/042636, Oct. 29, 2015.

Notification of Transmittal of the International Search Report and the Written Opinion of the International Searching Authority, or the Declaration, PCT/US2015/042015, Oct. 29, 2015.

Notification of Transmittal of the International Search Report and the Written Opinion of the International Searching Authority, or the Declaration, PCT/US2015/042035, Oct. 29, 2015.

Wood et al., "Active Motion Artifact Reduction for Wearable Sensors Using Laguerre Expansion and Signal Separation," Proceedings of the 2005 IEEE Engineering in Medicine and Biology, 27$^{th}$ Annual Conference, Shanghai, China, Sep. 1-4, 2005, pp. 3571-3574.

"U.S. Army Fitness Training Handbook" by the Department of the Army, 2003, The Lyons Press. p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2632 (1997).

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Colligan, M. J. et al. in "The psychological effects of indoor air pollution", Bulletin of the New York Academy of Medicine, vol. 57, No. 10, Dec. 1981, p. 1014-1026.

de Paula Santos, U. et al, in "Effects of air pollution on blood pressure and heart rate variability: a panel study of vehicular traffic controllers in the city of Sao Paulo, Brazil", European Heart Journal (2005) 26, 193-200.

(56) References Cited

OTHER PUBLICATIONS

Ebert, T et al., "Influence of Hydration Status on Thermoregulation and Cycling Hill Climbing," Med. Sci. Sport Exerc. vol. 39, No. 2, pp. 323-329, 2007.

European Search Report corresponding to European Application No. 07862660.3 dated Apr. 25, 2012; 7 pages.

Falkner et al, "Cardiovascular response to mental stress in normal adolescents with hypertensive parents. Hemodynamics and mental stress in adolescents," *Hypertension* 1:23-30.

Fitrainer "The Only Trainer You Need"; http://itami.com; Downloaded Feb. 26, 2010; © 2008 FiTrainer™; 2 pages.

Fleming et al., "A Comparison of Signal Processing Techniques for the Extraction of Breathing Rate from the Photopethysmorgram," World Academy of Science, Engineering and Technology, vol. 30, Oct. 2007, pp. 276-280.

Geladas et al., "Effect of cold air inhalation on core temperature in exercising subjects under stress," The American Physiological Society, pp. 2381-2387, 1988.

Gold, D.R. et al. in "Ambient Pollution and Heart Rate Variability", Circulation 2000, 101:1267-1273.

International Search Report and Written Opinion of the International Searching Authority, corresponding to PCT/US2012/0948079, mailed Oct. 9, 2012.

International Search Report and Written Opinion of the International Searching Authority, corresponding to PCT/US2007/025114, mailed May 13, 2008.

International Search Report Corresponding to International Application No. PCT/US2012/022634, Date of Mailing: Aug. 22, 2012, 9 pages.

Maomao et al., "Mobile Context-Aware Game for the Next Generation," $2^{nd}$ International Conference on Application and Development of Computer Games ADCOG 2003, p. 78-81.

Martins et al. "Zinc oxide as an ozone sensor" *Journal of Applied Physics* 96(3):1398-1408.

Maughan, R.J., "Impact of mild dehydration on wellness and on exercise performance," European Journal of Clinical Nutrition, 57, Suppl. 2, pp. S19-S23, 2003.

Maughan et al., "Exercise, Heat, Hydration and the Brain," Journal of the American College of Nutrition, vol. 26, No. 5, pp. 604S-612S, 2007.

Mostardi, R., et al., "The effect of increased body temperature due to exercise on the heart rate and the maximal aerobic power," Europ. J. Appl. Physiol, 33, pp. 237-245, 1974.

Nakajima et al., "Monitoring of heart and respiratory rates by photoplethyusmography using a digital filtering technique," Med. Eng. Phys., vol. 18, No. 5, Jul. 1996, pp. 365-372.

Notification of Transmittal of the International Search Report and Written Opinion of the International Search Authority issued Jul. 30, 2010 by the Korean Intellectual Property Office for corresponding International Application No. PCT/US2010/021936.

Notification of Transmittal of the International Search Report and Written Opinion of the International Search Authority issued Aug. 26, 2010 by the Korean Intellectual Property Office for corresponding International Application No. PCT/US2010/021629.

Notification of Transmittal of the International Search Report and the Written Opinion of the International Search Authority issued Sep. 16, 2010 by the Korean Intellectual Property Office for corresponding International Application No. PCT/US2010/024922.

Notification of Transmittal of the International Search Report and the Written Opinion of the International Search Authority issued Sep. 27, 2010 by the Korean Intellectual Property Office for corresponding International Application No. PCT/US2010/025216.

Notification of Transmittal of The International Search Report and The Written Opinion of the International Searching Authority, or the Declaration corresponding to International Application No. PCT/US2013/070271; Date of Mailing: Feb. 26, 2014; 13 pages.

Saladin et al. "Photosynthesis of $CH_4$ at a $TiO_2$ Surface from Gaseous $H_2O$ and $CO_2$," *J. Chem. Soc., Chem. Commun.* 533-534 (1995).

Shorten et al., "Acute effect of environmental temperature during exercise on subsequent energy intake in active men," Am. J Clin. Nutr. 90, pp. 1215-1221, 2009.

Skubal et al. "Detection and identification of gaseous organics using a $TiO_2$ sensor" *Journal of Photochemistry and Photobiology A: Chemistry* 148:103-108 (2002).

Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.

Thompson, M.W., "Cardiovascular drift and critical core temperature: factors limiting endurance performance in the heat?" J. Exerc. Sci. Fit, vol. 4, No. 1, pp. 15-24, 2006.

Zhang et al. "Development of Chemical Oxygen Demand On-Line Monitoring System Based on a Photoelectrochemical Degradation Principle" *Environ. Sci. Technol.*, 40(7):2363-2368 (2006).

Notification of Transmittal of the International Search Report and the Written Opinion of the International Searching Authority, or the Declaration, PCT/US2015/046079, Dec. 29, 2015.

Communication pursuant to Article 94(3) EPC, European Patent Application No. 13863449.8, Nov. 5, 2015, 7 pages.

Communication pursuant to Article 94(3) EPC, European Patent Application No. 14743615.8, Dec. 23, 2015, 7 pages.

Communication pursuant to Article 94(3) EPC, European Patent Application No. 14743839.4, Dec. 23, 2015, 6 pages.

International Search Report corresponding to International Patent Application No. PCT/US2012/046446; Date of Mailing: Jan. 14, 2013; 3 pages.

Communication pursuant to Article 94(3) EPC, European Patent Application No. 12820308.0, Feb. 3, 2016, 5 pages.

Notification of Transmittal of the International Search Report and Written Opinion of the International Search Authority issued May 26, 2016 by the Korean Intellectual Property Office for corresponding International Application No. PCT/US2016/019126.

Notification of Transmittal of the International Search Report and Written Opinion of the International Search Authority issued May 26, 2016 by the Korean Intellectual Property Office for corresponding International Application No. PCT/US2016/019132.

* cited by examiner

| Time of Day | Measured Value | % Multiplier | Resting Estimation |
|---|---|---|---|
| 7:00 AM | | 1 | |
| 9:00 AM | | 0.995918 | |
| 10:00 AM | | 0.992879 | |
| 12:00 PM | | 0.981398 | |
| 2:00 PM | | 0.983375 | |
| 4:00 PM | | 0.981398 | |
| 6:00 PM | 99.5°F | 0.981398 | 97.6°F |
| 8:00 PM | | 0.982386 | |
| 10:00 PM | | 0.985361 | |
| 12:00 AM | | 0.989457 | |
| 2:00 AM | | 1.000513 | |
| 4:00 AM | | 1.001848 | |
| 6:00 AM | | 1.002053 | |

Figure 10

APPARATUS AND METHODS FOR ESTIMATING TIME-STATE PHYSIOLOGICAL PARAMETERS

RELATED APPLICATION

This application is a 35 U.S.C. §371 national stage application of PCT Application No. PCT/US2012/046446, filed on Jul. 12, 2012, which claims the benefit of and priority to U.S. Provisional Patent Application No. 61/511,238 filed Jul. 25, 2011, the disclosures of which are incorporated herein by reference as if set forth in their entireties. The above-referenced PCT International Application was published in the English language as International Publication No. WO 2013/016007 on Jan. 31, 2013.

FIELD OF THE INVENTION

The present invention relates generally to monitoring apparatus and methods and, more particularly, to physiological monitoring apparatus and methods.

BACKGROUND OF THE INVENTION

Physiological parameters for living beings are typically a function of one or more of the following: the time-of-day, environmental conditions to which a being is exposed, activity level of a being, and various other physiological parameters. Many of these are related. For example, the average change in heart rate, body temperature, and heart rate variability (HRV) with the time-of-day are generally known based on human and animal studies of the circadian cycle.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a method of determining a value of a physiological parameter for a subject at a selected state (e.g., state of peak metabolism, state of lowered metabolism, state of rest, etc.), includes obtaining, via a device attached to the subject, a value of the physiological parameter of the subject at a particular time-of-day, and applying a time-dependent relationship function to the obtained physiological parameter value via at least one processor to determine a value of the physiological parameter at the selected state. Exemplary physiological parameters include, but are not limited to, subject body temperature, subject heart rate, subject heart rate variability, subject blood gas levels, subject metabolic rate, subject respiration rate, subject blood analyte levels, subject blood pressure, subject pulse pressure, etc. In some embodiments of the present invention, the time-dependent relationship function is derived from a circadian rhythm for the subject. In some embodiments of the present invention, the time-dependent relationship function is a lookup table.

In some embodiments of the present invention, determining a value of the physiological parameter of the subject at a selected state may include obtaining the value of the physiological parameter at the same time-of-day for multiple days and determining an average value for the multiple obtained values. Applying the time-dependent relationship function to the obtained physiological parameter value may include applying the time-dependent relationship function to the average value.

In some embodiments of the present invention, determining a value of a physiological parameter for a subject at a selected state may further include determining if the subject is in a condition of heightened activity at the selected time-of-day by determining via the device if at least one obtained physiological parameter value is at a level associated with the heightened activity condition. The time-dependent relationship function is adjusted for the heightened activity condition of the subject prior to determining a value of the physiological parameter at the selected state.

In some embodiments of the present invention, prior to obtaining a value of the physiological parameter of the subject at a particular time-of-day, values of the physiological parameter of the subject are obtained at multiple times during at least one previous day. A personalized time-dependent relationship function between at least one obtained value of the physiological parameter and a value of the physiological parameter at a time when the subject is at the selected state is generated for the subject using the obtained values from the at least one previous day. Applying the time-dependent relationship function to the obtained physiological parameter value includes applying the personalized time-dependent relationship function to the obtained physiological parameter value via at least one processor to determine a value of the physiological parameter at the selected state.

In some embodiments of the present invention, the time-dependent relationship function is adjusted for calories consumed by the subject prior to determining a value of the physiological parameter at a time when the subject is at the selected state.

In some embodiments of the present invention, the time-dependent relationship function is adjusted for blood oxygen level of the subject prior to determining a value of the physiological parameter at a time when the subject is at the selected state.

In some embodiments of the present invention, the device includes at least one physiological sensor that is configured to detect and/or measure physiological information from the subject to which the device is attached.

In some embodiments of the present invention, the device includes at least one environmental sensor that detects and/or measures environmental condition information in a vicinity of the subject. Determining a value of a physiological parameter for a subject at a selected state, according to some embodiments of the present invention, further comprises obtaining, via the device, a value of an environmental parameter in a vicinity of the subject at the particular time-of-day. Applying the time-dependent relationship function to the obtained physiological parameter value comprises applying the time-dependent relationship function and an environmental-dependent relationship function to the obtained physiological parameter value via the at least one processor to determine a value of the physiological parameter at a time when the subject is at the selected state.

Devices according to embodiments of the present invention may be configured to be attached to various portions of the body of a subject including, but not limited to, ear, arm, wrist, leg, hand, foot, finger, toe, chest, head, hair, nose, waist, trunk, shoulder, and neck. Devices according to embodiments of the present invention may also be configured to be embedded within clothing, foot apparel, and other wearable objects, without limitation. Additionally, devices according to embodiments of the present invention may be worn outside the body so as to be noninvasive, may be worn inside the body so as to be invasive, or may be worn subdermally so as to be mildly invasive.

According to other embodiments of the present invention, a method of determining a value of a physiological parameter (e.g., subject body temperature, subject heart rate, subject heart rate variability, subject blood gas levels, subject metabolic rate, subject respiration rate, subject blood analyte levels, subject blood pressure, and subject pulse pressure, etc.) for a subject at rest comprises obtaining, via a device attached to the subject, a value of the physiological parameter of the subject at a particular time-of-day, and applying a time-dependent relationship function to the obtained physiological parameter value via at least one processor to determine a value of the physiological parameter at a time when the subject is at rest.

In some embodiments of the present invention, determining a value of the physiological parameter of the subject at rest comprises obtaining the value of the physiological parameter at the same time-of-day for multiple days and determining an average value for the multiple obtained values. Applying the time-dependent relationship function to the obtained physiological parameter value may include applying the time-dependent relationship function to the average value.

In some embodiments of the present invention, determining a value of a physiological parameter for a subject at rest may further include determining if the subject is in a condition of heightened activity at the time-of-day by determining via the device if at least one obtained physiological parameter value is at a level associated with heightened activity. The time-dependent relationship function is adjusted for the heightened activity condition of the subject prior to determining a value of the physiological parameter at a time when the subject is at rest.

In some embodiments of the present invention, prior to obtaining a value of the physiological parameter of the subject at the time-of-day, values of the physiological parameter of the subject are obtained at multiple times during at least one previous day. A personalized time-dependent relationship function between at least one obtained value of the physiological parameter and a value of the physiological parameter at a time when the subject is at rest is generated for the subject using the obtained values from the at least one previous day. Applying the time-dependent relationship function to the obtained physiological parameter value includes applying the personalized time-dependent relationship function to the obtained physiological parameter value via the processor to determine a value of the physiological parameter at a time when the subject is at rest.

In some embodiments of the present invention, the time-dependent relationship function is adjusted for calories consumed by the subject prior to determining a value of the physiological parameter at a time when the subject is at rest.

In some embodiments of the present invention, the time-dependent relationship function is adjusted for blood oxygen level of the subject prior to determining a value of the physiological parameter at a time when the subject is at rest.

In some embodiments of the present invention, the device includes at least one environmental sensor that detects and/or measures environmental condition information in a vicinity of the subject. Determining a value of a physiological parameter for a subject at rest, according to some embodiments of the present invention, further comprises obtaining, via the device, a value of an environmental parameter in a vicinity of the subject at a particular time-of-day. Applying the time-dependent relationship function to the obtained physiological parameter value comprises applying the time-dependent relationship function and an environmental-dependent relationship function to the obtained physiological parameter value via at least one processor to determine a value of the physiological parameter at a time when the subject is at rest.

According to other embodiments of the present invention, a method of determining a value of a physiological parameter for a subject at a selected state (e.g., state of peak metabolism, state of lowered metabolism, state of rest, etc.) includes obtaining, via a device attached to the subject, a value of the physiological parameter (e.g., subject body temperature, subject heart rate, subject heart rate variability, subject blood gas levels, subject metabolic rate, subject respiration rate, subject blood analyte levels, subject blood pressure, and subject pulse pressure, etc.) of the subject at a selected time-of-day; obtaining, via the device, a value of an environmental parameter in a vicinity of the subject at the selected time-of-day via the environmental sensor; determining if the subject is in a condition of heightened activity at the selected time-of-day by determining via the device if at least one obtained physiological parameter value is at a level associated with heightened activity; and applying a time-dependent relationship function and an environmental-dependent relationship function to the obtained physiological parameter value via a processor to determine a value of the physiological parameter at the selected state, wherein the time-dependent relationship function is adjusted for the heightened activity condition of the subject prior to determining a value of the physiological parameter at the selected state.

In some embodiments of the present invention, obtaining a value of the physiological parameter of the subject at a particular time-of-day includes obtaining the value at the same time-of-day for multiple days and determining an average value for the multiple obtained values. Applying the time-dependent relationship function and the environmental-dependent relationship function to the obtained physiological parameter value includes applying the time-dependent relationship function and the environmental-dependent relationship function to the average value.

In some embodiments of the present invention, prior to obtaining a value of the physiological parameter of the subject at a particular time-of-day, values of the physiological parameter of the subject are obtained at multiple times during at least one previous day, and a personalized time-dependent relationship function between at least one obtained value of the physiological parameter and a value of the physiological parameter at the selected state is generated for the subject using the obtained values from the at least one previous day. Applying the time-dependent relationship function and the environmental-dependent relationship function to the obtained physiological parameter value includes applying the personalized time-dependent relationship function and the environmental-dependent relationship function to the obtained physiological parameter value via at least one processor to determine a value of the physiological parameter at the selected state.

In some embodiments of the present invention, the time-dependent relationship function is adjusted for calories consumed by the subject prior to determining a value of the physiological parameter at the selected state.

In some embodiments of the present invention, the time-dependent relationship function is adjusted for blood oxygen level of the subject prior to determining a value of the physiological parameter at the selected state.

According to other embodiments of the present invention, an apparatus includes a housing configured to be attached to a subject and at least one physiological sensor attached to the housing, wherein the at least one physiological sensor detects and/or measures physiological information from the subject. At least one processor may be attached to the housing or may be located remotely from the housing. The at least one processor is in communication with the at least one physiological sensor and is configured to obtain from the at least one physiological sensor a value of a physiological parameter of the subject at a particular time-of-day, and to apply a time-dependent relationship function to the obtained physiological parameter value to determine a value of the physiological parameter at a selected state.

In some embodiments of the present invention, the at least one processor is configured to obtain from the at least one physiological sensor the value of the physiological parameter at the same time-of-day for multiple days, determine an average value for the multiple obtained values, and apply the time-dependent relationship function to the average value.

In some embodiments of the present invention, the at least one processor is configured to determine if the subject is in a condition of heightened activity at the time-of-day by determining if at least one obtained physiological parameter value is at a level associated with heightened activity, and adjust the time-dependent relationship function for the heightened activity condition of the subject prior to determining a value of the physiological parameter at the selected state.

In some embodiments of the present invention, the at least one processor is configured to obtain values of the physiological parameter of the subject at multiple times during at least one previous day, generate a personalized time-dependent relationship function between at least one obtained value of the physiological parameter and a value of the physiological parameter at the selected state using the obtained values from the at least one previous day, and apply the personalized time-dependent relationship function to the obtained physiological parameter value to determine a value of the physiological parameter at the selected state.

In some embodiments of the present invention, the apparatus includes an environmental sensor that detects and/or measures environmental condition information in a vicinity of the subject. The at least one processor is configured to obtain a value of an environmental parameter in a vicinity of the subject at a particular time-of-day from the environmental sensor, and to apply the time-dependent relationship function and an environmental-dependent relationship function to the obtained physiological parameter value to determine a value of the physiological parameter at the selected state.

In some embodiments of the present invention, the at least one processor is configured to adjust the time-dependent relationship function for calories consumed by the subject prior to determining a value of the physiological parameter at the selected state.

In some embodiments of the present invention, the at least one processor is configured to adjust the time-dependent relationship function for blood oxygen level of the subject prior to determining a value of the physiological parameter at the selected state.

In some embodiments of the present invention, the housing is configured to be attached to an ear of the subject. In other embodiments, the housing is configured to be attached to one or more of the following portions of a body of a subject: arm, wrist, leg, hand, foot, finger, toe, chest, head, hair, nose, waist, trunk, shoulder, and neck. In other embodiments, the housing is configured to be embedded within clothing, foot apparel, and other wearable objects, without limitation.

Conventional methods and apparatus for studying the circadian cycle heretofore have not estimated resting state (or other) parameters of a being based on the current state of the being. There have been at least two major limitations preventing such an invention: 1) there has been no effort to estimate resting parameters based on what's already known about the relationships between resting state and current state and 2) there have been no apparatuses or methods for accurately and reliably measuring dynamically changing relationships between current and resting state parameters in everyday life activities.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 10 is an exemplary lookup table for estimating resting body temperature, according to some embodiments of the present invention.

DETAILED DESCRIPTION

Figure 1:
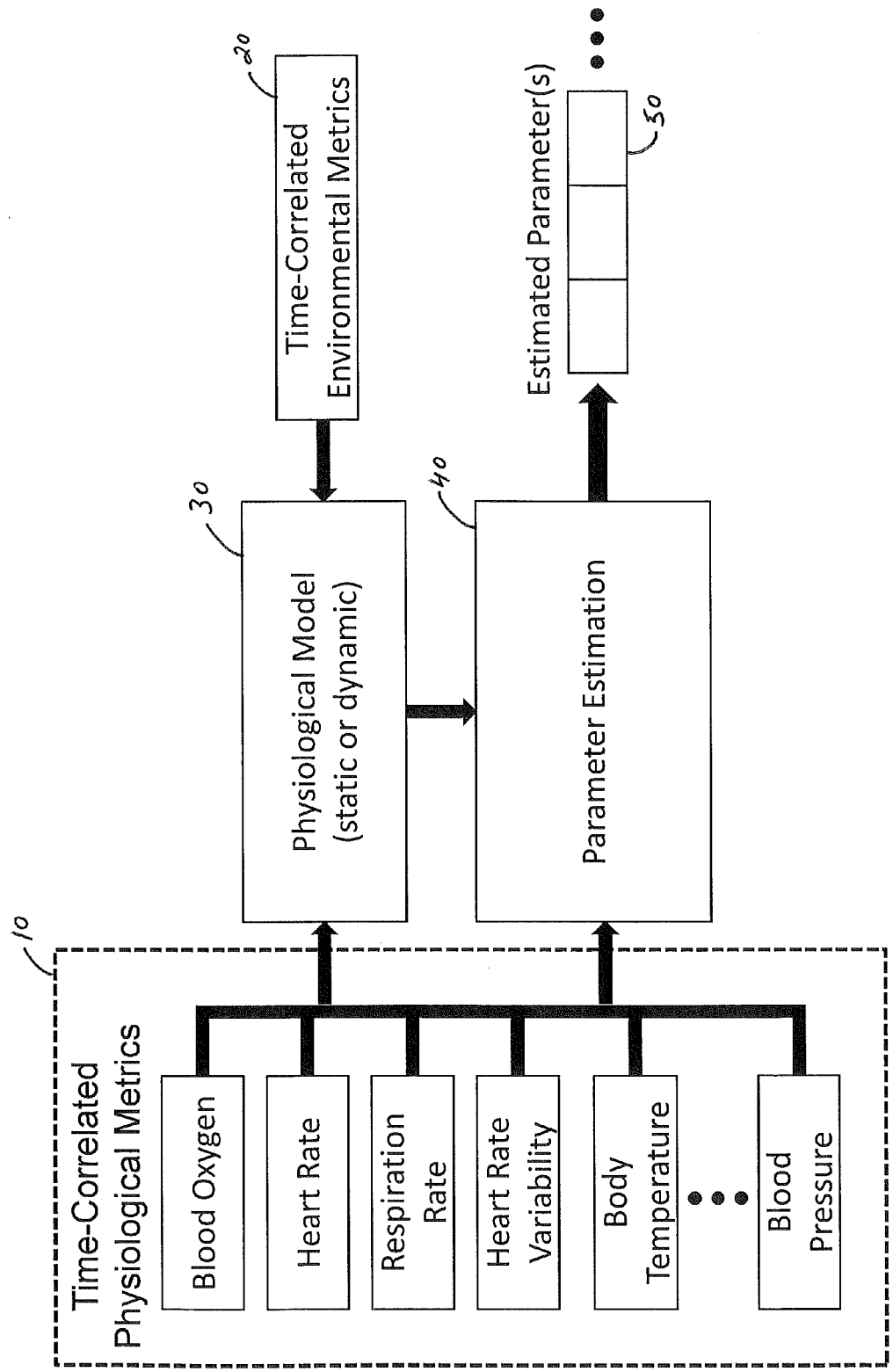
FIG. 1 is a block diagram of methods and apparatus for estimating physiological parameters of a being at a selected state, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "housing", as used herein, may refer to a physical structure for supporting and/or unifying one or more physical elements of the invention. For example, the housing of a wearable wrist sensor apparatus or headset sensor apparatus may comprise a structure to support the electronics, optics, and/or mechanical elements of the sensor. Two specific, non-limiting examples of a housing may be a "clamshell" of an earbud or one or more PCB boards for the sensor electronics. The structure may be composed of plastic, metal, polymer, ceramic, glass, composite material, or virtually any solid stable enough to support the physical elements of the apparatus.

The term "selected state", as used herein, includes, but is not limited to, state of peak metabolism, state of lowered metabolism, state of rest, a state of one's psychology or mental functioning or the body's physiology or physiological functioning. Any example of mental functioning may include psychosocial stress, mental stress, mental acuity, brain activity, conscious state, state or phase of sleep, or the like. An example of physiological functioning may include the functioning of one or more organs individually or in unison. In addition, a selected state may refer to a particular time of day where a particular or noteworthy mental or physiological event may take place.

The term "heightened activity condition", as used herein, includes, but is not limited to, elevated heart rate, elevated or lowered vital signs status, such as heart status (heart rate, ECG waveform intervals, cardiac output, cardiac stress or load, or the like), lung status (breathing rate, breathing volume, lung stress or load, or the like), blood pressure, blood oxygen level, heart rate variability, galvanic skin response, heat flux from the body, core body temperature, skin temperature, sympathetic or parasympathetic response, or the like.

The term "blood analyte" may refer to blood constituents, such as blood gases (blood oxygen, blood $CO_2$, blood hemoglobin, and the like), blood glucose, blood cholesterol, blood lactic acid, blood bilirubin, dissolved species in the blood, and the like.

The term "headset" includes any type of device or earpiece that may be attached to or near the ear (or ears) of a user and may have various configurations, without limitation. Headsets as described herein may include mono headsets (one earbud) and stereo headsets (two earbuds), earbuds, hearing aids, ear jewelry, face masks, headbands, and the like.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of embodiments of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature/subject (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells. Embodiments of the present invention are not limited to use by only humans.

The term "body" refers to the body of a subject (human or animal) who may wear a headset incorporating embodiments of the present invention.

The terms "being", "creature", "subject", and "organism", as used herein, are interchangeable and include, but are not limited to, humans and animals.

The terms "circadian rhythm" and "circadian cycle", as used herein, are interchangeable and refer to an endogenously driven, roughly 24-hour cycle in biochemical, physiological, or behavioral processes.

The term "processor" refers to a device that takes one form of information and converts this information into another form, typically having more usefulness than the original form. For example, in this invention, a signal processor may collect raw physiological and environmental data from various sensors and process this data into a meaningful assessment, such as pulse rate, blood pressure, or air quality. A variety of microprocessors or other processors may be used herein. The terms "signal processor", "processor", "controller", and "microcontroller", as used herein, are interchangeable.

Embodiments of the present invention provide methods and apparatus for estimating time-state physiological parameters/assessments, such as resting parameters, of a subject by factoring functional relationships between the time-dependent parameters and other measured factors. For example, current state parameters (such as vital signs, environmental exposures, time-of-day, and the like) are measured and a physiological model is applied to generate an estimation of resting state parameters (or other particular states) of the subject. These relationships can be static relationships based on models that apply knowledge of how a current state of the subject relates to a resting state of the subject. These relationships can also be dynamic relationships based on personalized monitoring of a subject throughout various life activities.

Figure 2:
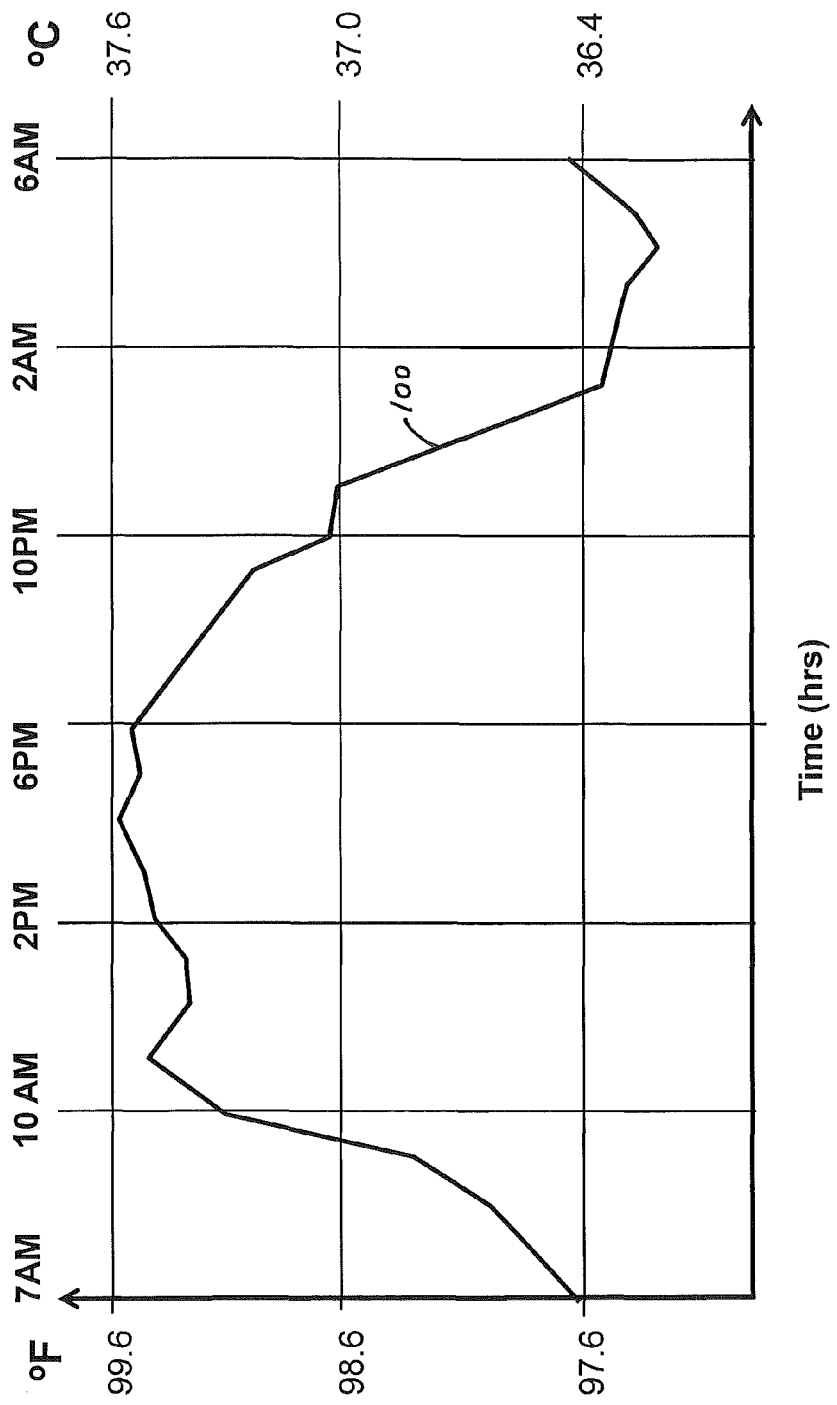
FIG. 2 is an exemplary plot of how tympanic or core body temperature may change with time-of-day for an average person.
Figure 7:
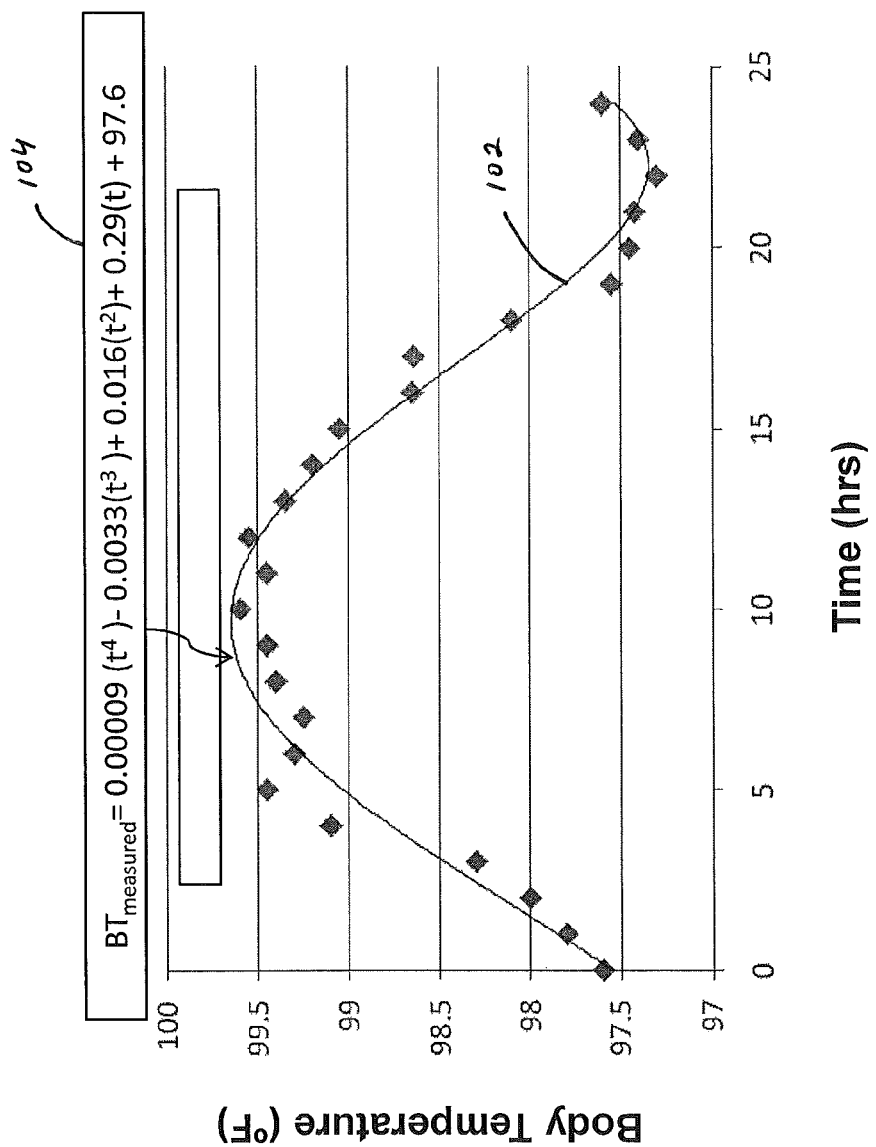
FIG. 7 is a plot of average body temperature vs. time calculated using a polynomial equation for body vs. time-of-day, according to some embodiments of the present invention.

Average body temperature, heart rate, heart rate variability for a subject, as well as many other vital parameters, change throughout the day on a regular schedule dependent on the time-of-day, consistent with normal circadian rhythms. Additionally, average values of vital signs will change throughout the day based on changes in a subject's physical activity or metabolic rate. As shown in FIGS. 2 and 7, average body temperature for a human subject may change by ~2° F. from early morning to mid-day. In FIG. 2, body temperature is plotted on the y-axis and time in hours is plotted on the x-axis. Curve 100 in FIG. 2 is a plot of average core body temperature vs. time for an average human over an average day. In FIG. 7, body temperature is plotted on the y-axis and time in hours is plotted on the x-axis. Polynomial equation 104 is used to calculate the plot 102.

Figure 3:
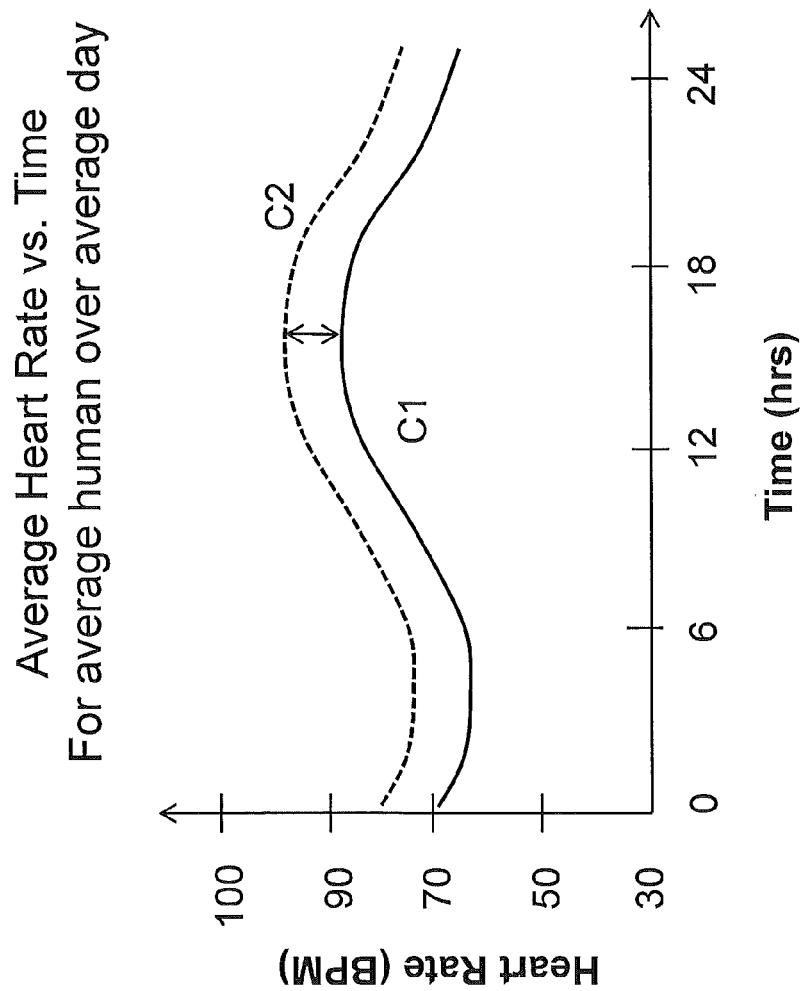
FIG. 3 is an exemplary plot of how heart rate may change with time-of-day for an average person, wherein curve C1 represents a normal cycle and wherein curve C2 represents an elevated cycle.

Similarly, as shown in FIG. 3, average heart rate for a human subject may change by ~15 BPM (beats per minute) during that same period. FIG. 3 illustrates how heart rate may change with time-of-day for an average person, wherein curve C1 represents a normal cycle and wherein curve C2 represents an elevated cycle. In FIG. 3, heart rate is plotted on the y-axis and time in hours is plotted on the x-axis. Thus, if average body temperature and average heart rate are being monitored throughout the day, estimating resting body temperature and resting heart rate for a subject may be derived by applying the respective relationships to the existing measured state.

For example, if the current state at mid-day shows a body temperature of 99.6° F. and heart rate of 80 BPM, the resting state values may be estimated as 97.6° F. and 65 BPM, by subtracting 2° F. from body temperature and 15 BPM from heart rate, respectively. Percent (%) change relationships for estimating resting state, as opposed to absolute value changes, may also be used to estimate resting state. For example, the change from current state to resting state in the aforementioned case is ~2% and 18% for body temperature and resting heart rate, respectively. Thus, a lookup table (e.g., table 110, FIG. 10) may be generated with time-of-day in one column, measured value in a second column, and the associated percent multiplier in a third column, where the percent multiplier is the ratio between resting value and measured value. The estimation for resting value can then be generated by multiplying this time-of-day-dependent ratio by the measured vital parameter at the given time-of-day of the measurement.

A specific example for the case of body temperature is presented in FIG. 10, using the same relationships and data of FIG. 2, where a measurement of body temperature has been made at 6 PM, with a multiplier of ~0.981, yielding a resting body temp estimate of 97.6° F. A complimentary lookup table may replace the % multiplier column with a ±add/subtract column, where the ±number is the amount to add or subtract from the measured value to generate an estimate of the resting value.

It should also be noted that a formula, rather than a lookup table, may also be used to relate resting estimates to measured estimates, depending on the time-of-day. For example, a polynomial formula representing the table of FIG. 10 may be: Estimated Resting Value=(Measured Value)*$(-0.29x^4+0.79x^3-0.63x^2+0.13x+1.0)$, where x=time in hours, starting at x=0 for 7 AM. It is apparent from this formula that at 7 AM (x=0), the Estimated Resting Value=Measured Value, which is expected in the aforementioned formalism.

Figure 4:
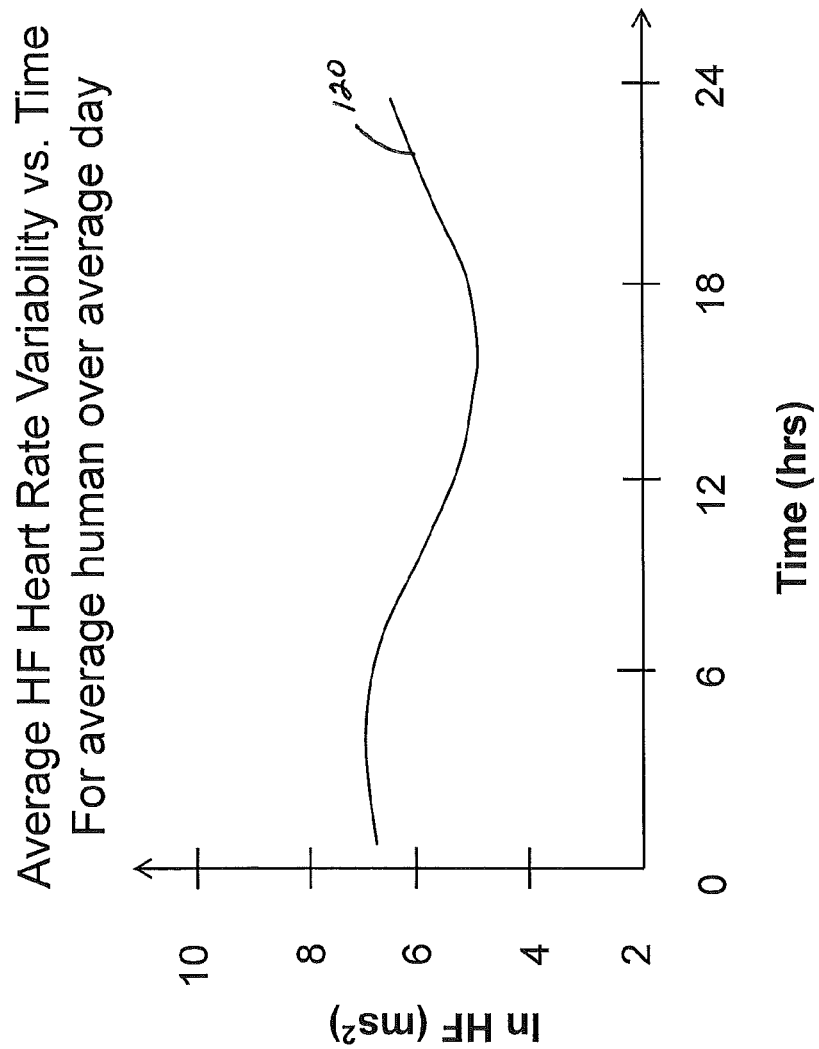
FIG. 4 is an exemplary plot of how heart rate variability (HRV) may change with time-of-day for an average person.

FIG. 7 shows an exemplary plot 102 of average human body temperature during a day, along with an approximate functional relationship for average body temperature vs. time. In the illustrated embodiment, the functional relationship is a polynomial equation 104 of order n=4. The $a_0$ term is 97.6° F., representing the resting body temperature, or $BT_{resting}$=97.6° F. If a person's resting body temperature ($BT_{resting}$) had started higher or lower than 97.6° F., the polynomial equation may still hold, with the only substantial difference being the $a_0$ term for $BT_{resting}$. Thus, an equation for estimating $BT_{resting}$ vs. $BT_{measured}$ may be derived by rearranging terms such that $a_0=BT_{resting}=BT_{measured}-[9E-05(t^4)-0.0033(t^3)+0.0161(t^2)+0.2868(t)]$. More generally, $a_0=BT_{resting}=BT_{measured}-[a_n(t^n)+a_{n-1}(t^{n-1}a_{n-2}(t^{n-2})+ \ldots + a_1(t)]$, where "n" is the order of the polynomial equation and where t=0 represents the value of BT at the resting state. The second term in the brackets may be related to body temperature changes due to circadian rhythms, such that $BT_{resting}=BT_{measured}-\Delta BT_{circadian}$. This same general relationship may be applied towards heart rate (HR) as shown in FIG. 3 and heart rate variability in FIG. 4. In FIG. 4, heart rate variability is plotted on the y-axis and time in hours is plotted on the x-axis. The units along the y-axis are milliseconds-squared. Plot 120 illustrates how heart rate variability (HRV) may change with time-of-day for an average person. For example, $HR_{resting}=HR_{measured}-\Delta HR_{circadian}$ and $HRV_{resting}=HRV_{measured}\ HRV_{circadian}$. This formalism may be applied towards blood oxygen ($SPO_2$), respiration rate (RR), blood pressure (BP), pulse pressure (PP), and other vital parameters (VP), that may change regularly throughout the day according to $VP_{resting}=VP_{measured}-\Delta VP_{circadian}$.

In some embodiments of the present invention, the general relationships illustrated in FIGS. 2, 3, and 7 may not enable a prediction of resting state (or other selected state) as accurately as desired. For example, a person engaging in heightened activity or personal variations may cause substantial departures from the general relationships. Fortunately, these differences may effectively average out if vital signs measurements are made over a period of time. For example, if a vital sign of interest is measured over several days at the same time-of-day, during different activity levels, the average value of the vital sign may be largely divorced of convolutions caused by heightened or acute activity. This average value of $VP_{measured}$ may then be used to estimate $VP_{resting}$. However, it may be difficult to measure the vital parameter at the same time-of-day for multiple days, and a one-time measurement of a vital parameter taken during or following high activity may not be sufficient to support an accurate estimate of the resting value, using the general relationships alone.

Figure 5:
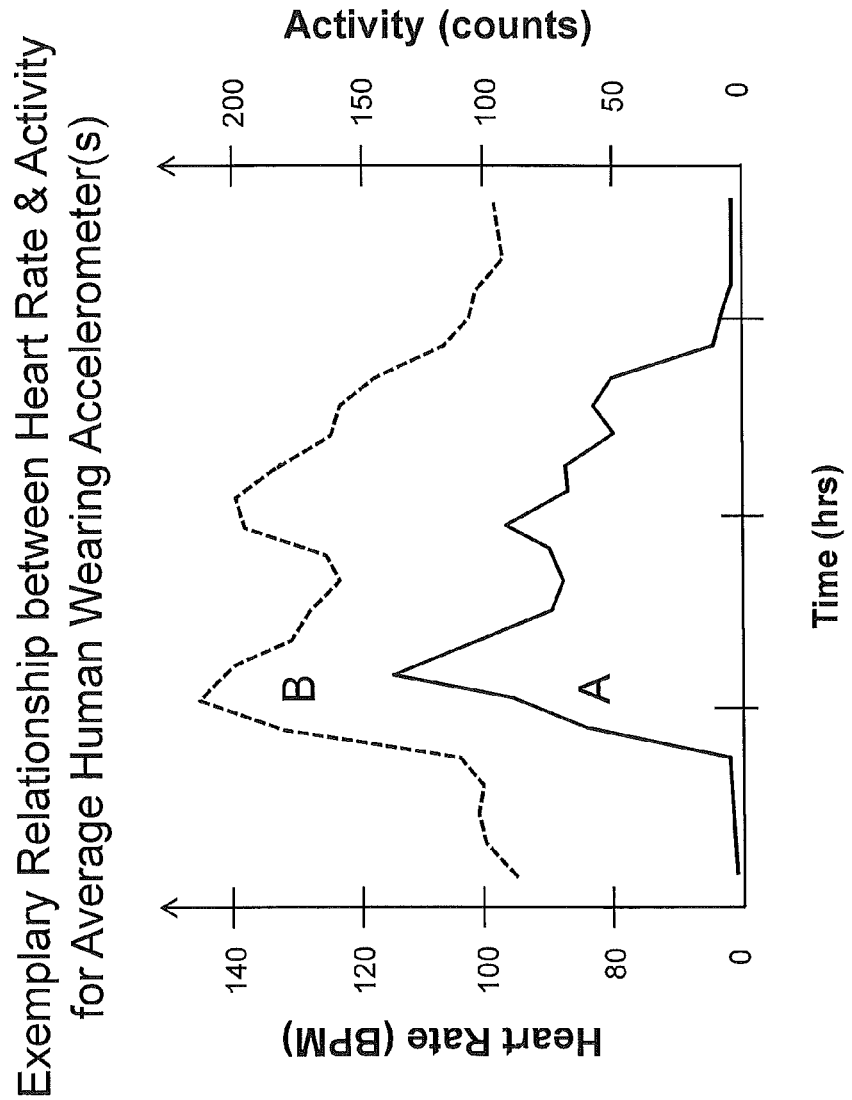
FIG. 5 is an exemplary plot of how heart rate of a person may change with the person's activity level.

To correct for conditions of high activity, a general relationship between changes in activity and changes in vital parameters may be used to correct an estimate of resting parameters, according to some embodiments of the present invention. For example, during activity, the heart rate of a subject may increase in a predictable fashion, as shown in FIG. 5. In FIG. 5, heart rate is plotted on the left y-axis, activity is plotted on the right y-axis, and time in hours is plotted on the x-axis. Curve A in FIG. 5 illustrates heart rate and activity for a person at a first state, and curve B in FIG. 5 illustrates heart rate and activity for the person at a heightened activity state.

Generally, as illustrated in FIG. 5, heart rate will increase with activity, and the rate of increase with activity may be proportional to the physical fitness or aerobic capacity ($VO_2$max) of the subject. Thus, if the relationship between heart rate and activity is known for a subject, then the differential increase in heart rate due to elevated activity, for a particular time-of-day, may be subtracted from the current heart rate measurement. Namely, the estimated resting heart rate can be defined as $HR_{resting}=HR_{measured}-\Delta HR_{circadian}-\Delta HR_{activity}$, where $\Delta HR_{activity}$ is the change in heart rate with activity (either positive/negative for increases/decreases in heart rate with activity). For other vital parameters, the term $\Delta VP_{activity}$ may be used instead.

Personal differences between individuals may cause deviations from the general, "universal" relationships previously described. For example, subjects having a higher metabolic rate change throughout a given day may have a larger total value or percent change in vital parameters between early morning and midday. Improving the accuracy of estimating resting parameters can be achieved by measuring vital parameters throughout the day, generating average time-dependent relationships based on these measured parameters, and deriving a personalized time-dependent relationship between measured and resting parameters. Once a personalized, functional, time-dependent relationship is generated between measured (current state) vital parameters and resting state vital parameters, this model may be used to estimate resting state parameters by inputting current state measurements into the model. For current state measurements taken at high activity, stored relationships between a subject's vital parameters and activity can be employed to subtract the change in vital parameter values with activity ($\Delta VP_{activity}$) as with the heart rate example described above.

Environmental exposures (i.e., environmental conditions to which a subject is exposed) may also affect the time-dependent relationship between measured and resting parameters. For example, sunlight exposure may elevate metabolism, resulting in an increase in heart rate, breathing, rate, other vital parameters, or the like. In such case, it may be insufficient to estimate resting parameters by simply measuring current resting parameters and inputting current parameters into the functional model. Rather, it may be more accurate to estimate resting vital parameters according to $VP_{resting}=VP_{measured}-\Delta VP_{circadian}-\Delta VP_{environmental\ exposure}$ where $\Delta VP_{environmental\ exposure}$ is the change (positive or negative) in the vital parameter value due to environmental exposure (e.g., sunlight exposure, etc.). A change in vital parameters may be caused by many different forms of environmental exposures such as, but not limited to, loud noises, strong wind, extreme temperatures, short wavelength light (e.g., light at wavelengths <470 nm), airborne pollution, mechanical stress, and the like.

It should be noted that multiple parameters may simultaneously affect the relationship between resting values and measured values. For example, if physical activity and environmental exposure both have an impact on instantaneous vital parameters, then a more general relationship for resting vital parameters may be: $VP_{resting}=VP_{measured}-\Delta VP_{circadian}-\Delta VP_{activity}-\Delta VP_{environmental\ exposure}$. Additional relationships, such as changes in a vital parameter with food intake (calories consumed), blood oxygen ($SPO_2$), and the like may also be incorporated. These additional relationships can be accommodated by $\Delta VPn$, where the integer "n" represents an additional factor which may affect $VP_{measured}$.

The aforementioned models for estimating resting parameters have been presented as "static" models. A static model, once implemented or derived, stays fixed with time. However, models for determining a value of a physiological parameter for a subject at a selected state (e.g., at rest, etc.), according to some embodiments of the present invention, may also be dynamic, changing with time based on updated information about a particular person or group of people. For example, a person undergoing cardiac therapy, a new diet, drug therapy, or other lifestyle change may see an acute or chronic change in metabolism over time. In such case, static models may be insufficient for estimating resting parameters from current state measured parameters. Rather, it may be more accurate to measure vital parameters over a period of time and update the model based on updated relationships between resting and current state parameters.

Figure 8:
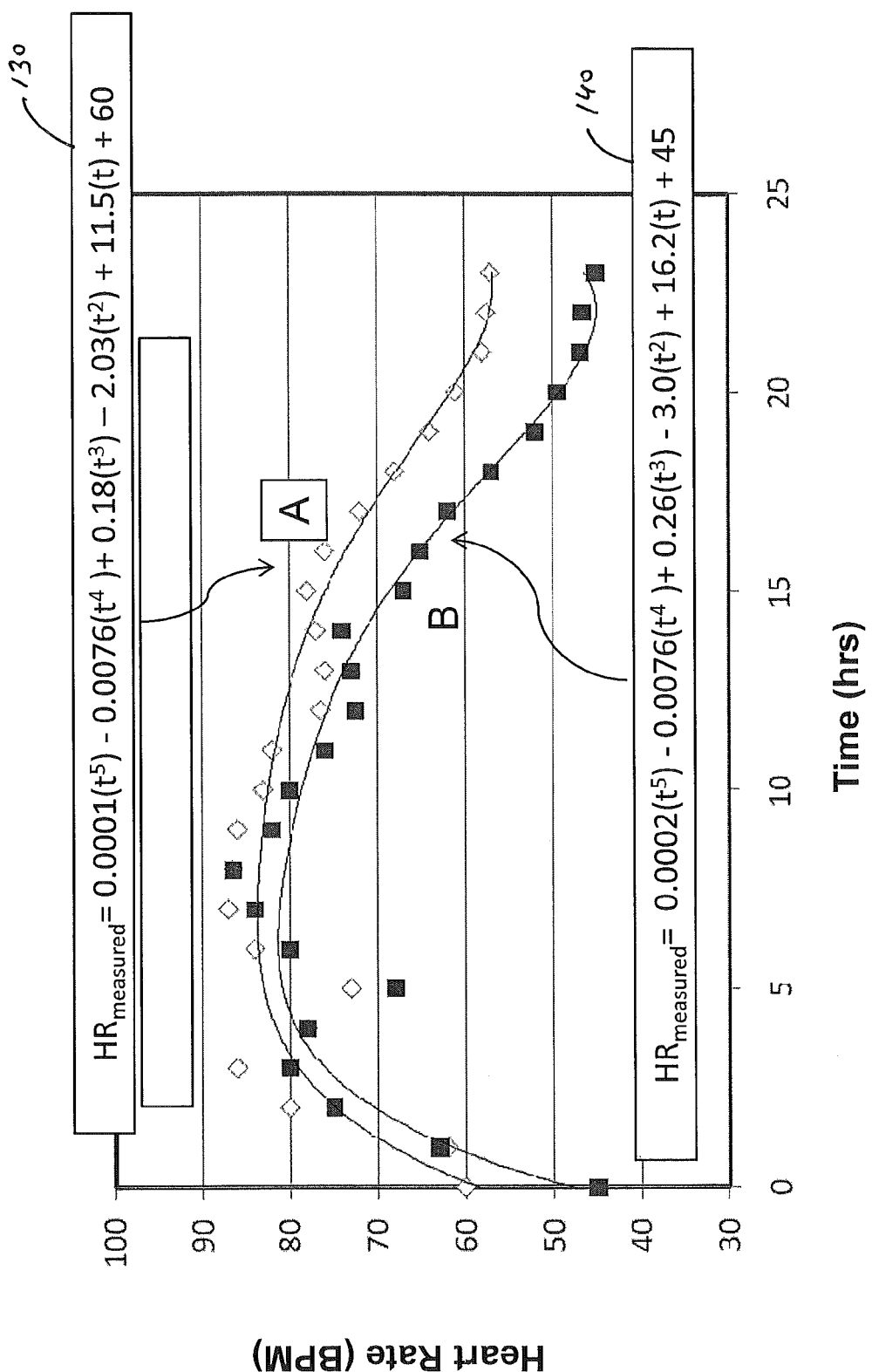
FIG. 8 is a plot of heart rate vs. time for an average person, wherein curve (A) represents heart rate vs. time before a lifestyle change, wherein curve (B) represents heart rate vs. time after a lifestyle change, and wherein curve (A) and (B) are generated via respective polynomial equations according to some embodiments of the present invention.

FIG. 8 shows a specific example of a dynamic model for determining a value of a physiological parameter for a subject at a selected state (e.g., at rest, etc.) according to some embodiments of the present invention. FIG. 8 is a graph of heart rate vs. time-of-day for a twenty-four hour (24 hr) period. Curves A and B in FIG. 8 show the circadian change in average heart rate profile of an average person before and after a lifestyle change. Polynomial representations of these plots are also shown, with a polynomial order of n=5. Polynomial equation 130 is used to generate curve A in FIG. 8 and polynomial equation 140 is used to generate curve B in FIG. 8.

As illustrated in FIG. 8, after the lifestyle change, the average heart rate changes more dramatically as the time-of-day changes, as exemplified by the 2× increase in the 5th-power coefficient in the "B" curve when compared with the "A" curve. The resting heart rate for each case is the $a_0$ terms of each, 60 and 45 BPM for curves A and B, respectively. Because the change in each model (for curves A and B) is not merely a scalar addition or subtraction, accurately estimating resting heart rate may require measuring average heart rate throughout the day, over the course of several days, modeling a relationship between resting and current state parameters, and then inputting current state parameters into the model. In one embodiment of the present invention, the model may be a polynomial equation fit to the measured data, as shown in FIG. 8. However, other models may be employed to improve accuracy or model simplicity, according to embodiments of the present invention.

FIG. 1 is a block diagram of methods and apparatus for generating estimated physiological parameters of a subject at a selected state based on current state measurements, according to some embodiments of the present invention. Time-correlated physiological metrics (Block 10) and/or time-correlated environmental metrics (Block 20) are collected and are input into a physiological model (static, dynamic, or a combination of both) (Block 30), and the desired parameters (such as resting state parameters) are estimated (Block 40) based on the metrics and physiological model. The estimated parameters are then reported in an organized fashion (Block 50).

Figure 6:
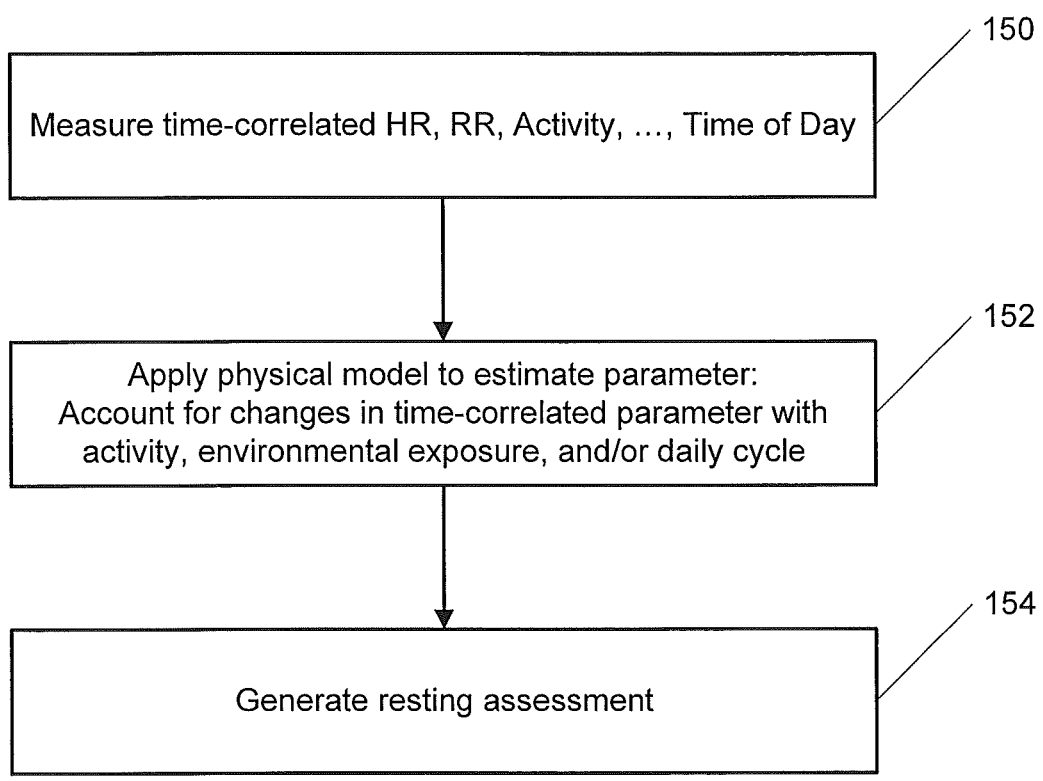
FIG. 6 is a flow chart for an algorithm for estimating resting parameters, according to some embodiments of the present invention.

An algorithm for estimating a resting parameter according to embodiments of the present invention is presented in the flow chart of FIG. 6. The algorithm includes measuring time-correlated heart rate (HR), respiration rate (RR), activity levels, etc., at a particular time of day (Block 150). A physical model is applied to estimate a parameter value that accounts for changes in the time-correlated parameter with activity, environmental exposure, and/or daily cycle (Block 152). A resting assessment is then generated (Block 154).

Figure 11:
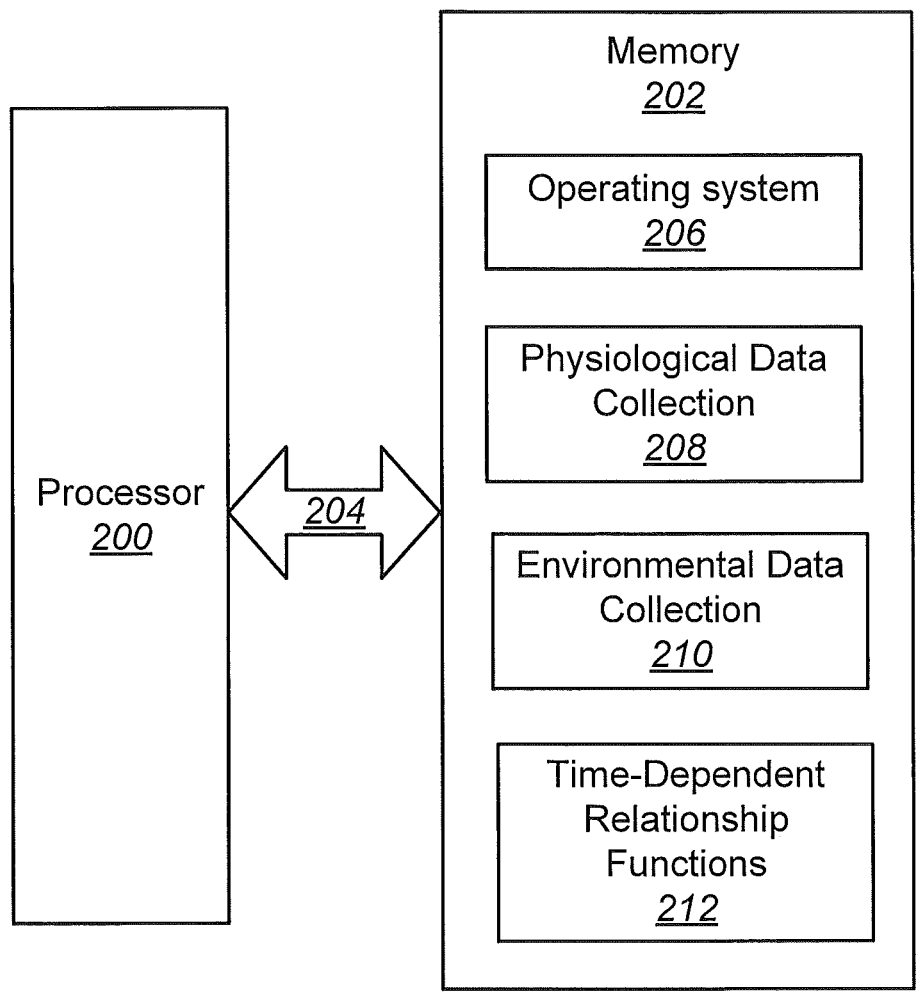
FIG. 11 is a block diagram that illustrates details of an exemplary processor and memory that may be used in accordance with embodiments of the present invention.

FIG. 11 illustrates an exemplary processor 200 and memory 202 that may be used in a wearable device and/or a device remote from a subject to carry out various embodiments of the present invention. The processor 200 communicates with the memory 202 via an address/data bus 204. The processor 200 may be, for example, a commercially available or custom microprocessor or similar data processing device. The memory 202 is representative of the overall hierarchy of memory devices containing the software and data used to perform the various operations described herein. The memory 202 may include, but is not limited to, the following types of devices: cache, ROM, PROM, EPROM, EEPROM, flash, SRAM, and DRAM.

As shown in FIG. 11, the memory 202 may hold various categories of software and data: an operating system 206, a physiological data collection module 208, an environmental data collection module 210, and a time-dependent relationship function module 212. The operating system 206 controls operations of the physiological and environmental sensors.

It should be noted that estimating a physiological metric at a selected time state need not necessarily require a direct measurement of current time. For example, if the relationship between at least one physiological parameter and time is already known, or if that relationship is developed by recording data for a subject wearing a physiological sensor over time as shown in FIG. 11, then the current time may be inferred through this relationship and factored into an estimate for a second physiological metric at a selected time state. For example, if the relationship between the subject's core body temperature over time is known (as shown in FIG. 2), then a subject's HRV may be estimated for a selected time-state by estimating the current time based on the measured core body temperature at a current state. In such case, the current time need not be measured. However, in such case, because the current time is inferred and not directly noted or measured, it may be further beneficial to measure the subject's activity and have this factored into the relationship function 212 (as discussed for FIG. 5) so as to prevent activity-based artifacts from causing inaccurate estimates of a second physiological metric at a selected state.

The physiological data collection module 208 comprises logic for obtaining from a physiological sensor a value of a physiological parameter of a subject at a particular time-of-day. The physiological data collection module 208 may also comprise logic for obtaining from a physiological sensor the value of a physiological parameter at the same time-of-day for multiple days, and logic for determining an average value for the multiple obtained values. The physiological data collection module 208 may also comprise logic for obtaining values of a physiological parameter of a subject at multiple times during at least one previous day.

The environmental data collection module 210 comprises logic for obtaining from an environmental sensor a value of an environmental parameter in a vicinity of a subject at a particular time-of-day.

The time-dependent relationship function module 212 comprises logic for applying a time-dependent relationship function to an obtained physiological parameter value to determine a value of the physiological parameter at a selected state, and logic for applying the time-dependent relationship function and an environmental-dependent relationship function to an obtained physiological parameter value (and average value) to determine a value of the physiological parameter at the selected state. In addition, the time-dependent relationship function module 212 may comprise logic for determining if a subject is in a condition of heightened activity at a selected time-of-day by determining if at least one obtained physiological parameter value is at a level associated with heightened activity, and may comprise logic for adjusting the time-dependent relationship function for the heightened activity condition of the subject prior to determining a value of the physiological parameter at the selected state. The time-dependent relationship function module 212 may comprise logic for generating a personalized time-dependent relationship function between a measured value of a physiological value and a value of the physiological parameter at a selected state using obtained values from at least one previous day, and may comprise logic for applying the personalized time-dependent relationship function to a obtained physiological parameter value to determine a value of the physiological parameter at the selected state.

The time-dependent relationship function module 212 may also comprise logic for adjusting a time-dependent relationship function for calories consumed by a subject prior to determining a value of the physiological parameter at a selected state. The time-dependent relationship function module 212 may also comprise logic for adjusting a time-dependent relationship function for blood oxygen level of a subject prior to determining a value of the physiological parameter at a selected state.

According to some embodiments of the present invention, collecting measured time-dependent metrics may be manual or automatic. Records can be taken over time, recorded, and processed into time-dependent relationships by skilled professionals or personal recording. However, it may be easier to record this data with one or more wearable devices having multiple wearable sensors. For example, wired and wireless vital parameter modules may be located along several parts of the body, or integrated into a single device worn at a single place along the body. These wearable devices may measure vital parameters throughout the day and, with microprocessors or other processing devices, generate estimations for resting parameters. Memory devices, such as memory chips, data storage devices, and the like, may be used to store and update physiological models according to embodiments of the present invention, and at least one processor may be used to estimate parameters based on the metrics and model. At least one processor may also be used to organize the data into a string of outputs for each measured parameter. There is great flexibility in the electronics that may be used to implement embodiments of the present invention. Individual electronic components or chips may be used and integrated within circuit board, or the electronics may integrate memory storage, data processing, and data translation within a single chip, or other combinations or electronics configurations may be used.

Some types of wearable devices may be more suited for sensor integration than other devices. For example, an ear-worn device may be especially suited for measuring blood flow, heart rate, breathing rate, EEG, and body temperature, due in part to the location of the ear with respect to physiological structures such as the carotid artery, capillaries, ear blood vessels, the brain, and the tympanic membrane. However many other form-factors for a single wearable device may be employed. For example, strong blood flow and heat generation in the limbs, digits, and torso enable integrated sensor locations in the arms, wrist, legs, hands, feet, fingers, toes, chest, head, hair, nose, waist, trunk, shoulder, neck, and other locations. Furthermore, physiological and environmental sensors may be embedded in clothing or other wearable devices, such as headsets, earbuds, wrist watches, adhesive patches, rings, bracelets, necklaces, footwear, socks, shirts, pants, underwear, earrings and other body piercings, hats, glasses, and the like.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Wireless, Bluetooth®-enabled, and/or other personal communication headsets may be configured to incorporate physiological and/or environmental sensors, according to some embodiments of the present invention. As a specific example, Bluetooth® headsets are typically lightweight, unobtrusive devices that have become widely accepted socially. Moreover, Bluetooth® headsets are cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of headsets include, but are not limited to accelerometers, auscultatory sensors, pressure sensors, humidity sensors, color sensors, light intensity sensors, pressure sensors, etc.

Optical coupling into the blood vessels of the ear may vary between individuals. As used herein, the term "coupling" refers to the interaction or communication between excitation light entering a region and the region itself. For example, one form of optical coupling may be the interaction between excitation light generated from within a light-guiding earbud and the blood vessels of the ear. Light guiding earbuds are described in co-pending U.S. Patent Application Publication No. 2010/0217102, which is incorporated herein by reference in its entirety. In one embodiment, this interaction may involve excitation light entering the ear region and scattering from a blood vessel in the ear such that the intensity of scattered light is proportional to blood flow within the blood vessel. Another form of optical coupling may be the interaction between excitation light generated by an optical emitter within an earbud and the light-guiding region of the earbud.

Embodiments of the present invention are not limited to headsets and devices that communicate wirelessly. In some embodiments of the present invention, headsets and devices configured to monitor an individual's physiology and/or environment may be wired to a device that stores and/or processes data. In some embodiments, this information may be stored on the headset itself.

Figure 9:
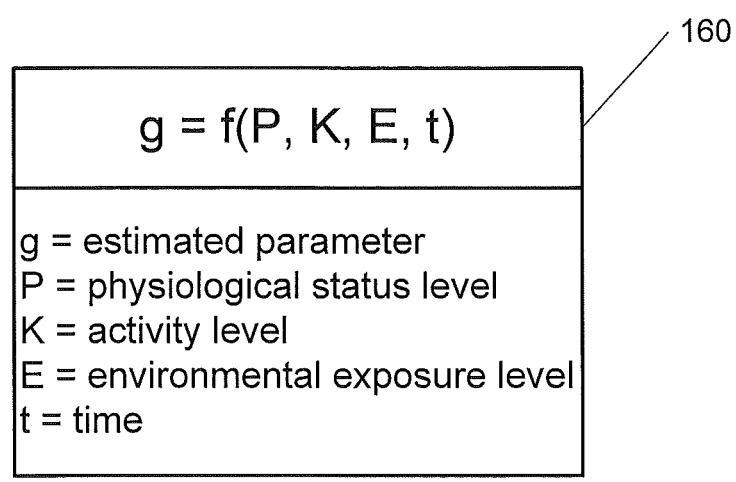
FIG. 9 illustrates a functional relationship between an estimated parameter and multiple time-dependent inputs, according to some embodiments of the present invention.

Embodiments of the present invention may apply to the estimation of parameters at another state (other than resting state) by measuring current state parameters and processing this data via a model to generate an estimate of parameters at the desired state. For example, embodiments of the present invention may be applied to estimating vital parameters at the state of peak metabolism during midday. In another example, embodiments of the present invention may be applied to estimating vital parameters at the state of lowered metabolism associated with evening time, for example, just before bedtime. A more general model or equation 160 for estimating vital parameters at a desired state is presented in FIG. 9.

It should also be understood that user input may be used to improve the accuracy of resting state (or other state) parameters. For example, relationships may exist between resting vs. measured parameters and weight, gender, height, habitual information, and the like. A particular example of habitual information may be the time-of-day someone wakes up in the morning. For example, the time of waking up may replace "7 AM" shown in FIG. 2.

Methods for estimating a physiological parameter at a selected state, according to some embodiments of the present invention, may be applied to wearable sensors as well as nonwearable sensors capable of measuring one or more physiological parameters and physical activity in a time-correlated manner, during enough times of the day to build or execute a time-correlated model. For example, whereas multiple examples of wearable devices have been described herein, alternative embodiments may employ wall-mounted sensors, bed-mounted sensors, car-mounted sensors, portable sensors, or other sensor configurations that can measure physiological parameters or physical activity at a "stand-off" distance from a subject. As a specific example, a wall-mounted camera may be configured to measure the heart rate, breathing rate, and physical activity of a subject and to record a time stamp of that subject. Measuring heart rate or breathing rate with a mounted camera may be achieved via algorithms capable of assessing individual video frames for changes in the chest size in time or by detecting certain wavelengths of light associated with heat changes, for example. Additionally, physical activity may be assessed by algorithms capable of identifying subjects and subject motion and translating this identified motion to activity level. In such case, a time-correlated relationship function may be generated for the subject. Thus, the heart rate or respiration rate of the subject may be accurately estimated for a selected state, such as a resting state or other state, when the subject is not in view of the camera by applying the time-correlated relationship function for the subject at the selected state. Suitable stand-off detection methods may employ, for example, electromagnetic, electrical, magnetic, inductive, capacitive, thermal, acoustic, or other energy detection techniques. For example, the heart rate, breathing rate, and activity of a subject sleeping in a bed, and coupled to a stand-off capacitive or inductive sensor, may be monitored through changes in capacitance or inductance. If this data is time-stamped by a processor, the inventive aspects described herein may be applied for determining one or more physiological parameters for that subject at a selected state, such as a state of reduced or elevated activity.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of estimating a value of a physiological parameter for a subject at a selected metabolic state, the method comprising:
   obtaining, via a device attached to the subject, a value of the physiological parameter of the subject at a time-of-day, wherein the device comprises a physiological sensor, wherein the physiological sensor detects and/or measures physiological information from the subject; and
   estimating the value of the physiological parameter for the subject at the selected metabolic state by applying a time-dependent relationship function to the obtained physiological parameter value via at least one processor, wherein the selected metabolic state is different from a current metabolic state of the subject.

2. The method of claim 1, wherein the time-dependent relationship function is derived from a circadian rhythm for the subject.

3. The method of claim 1, wherein the time-dependent relationship function is a lookup table.

4. The method of claim 1, wherein the physiological parameter includes one or more of the following: subject body temperature, subject heart rate, subject heart rate variability, subject blood gas levels, subject metabolic rate, subject respiration rate, subject blood analyte levels, subject blood pressure, and subject pulse pressure.

5. The method of claim 1, wherein estimating the value of the physiological parameter for the subject at the selected metabolic state comprises obtaining the value of the physiological parameter at the same time-of-day for multiple days and determining an average value for the multiple obtained values, and wherein applying the time-dependent relationship function to the obtained physiological parameter value comprises applying the time-dependent relationship function to the average value.

6. The method of claim 1, further comprising determining if the subject is in a condition of heightened activity at the time-of-day by determining via the device if at least one obtained physiological parameter value is at a level associated with heightened activity, and wherein the time-dependent relationship function is adjusted for the heightened activity condition of the subject prior to estimating the value of the physiological parameter at the selected metabolic state.

7. The method of claim 1, wherein prior to obtaining a value of the physiological parameter of the subject at the time-of-day, values of the physiological parameter of the subject are obtained at multiple times during at least one previous day, and a personalized time-dependent relationship function between at least one of value of the physiological parameter and a value of the physiological parameter at the selected metabolic state is generated for the subject using the obtained values from the at least one previous day, and wherein applying the time-dependent relationship function to the obtained physiological parameter value comprises applying the personalized time-dependent relationship function to the obtained physiological parameter value via the processor to estimate the value of the physiological parameter at the selected metabolic state.

8. The method of claim 1, wherein the device further includes an environmental sensor that detects and/or measures environmental condition information in a vicinity of the subject, and further comprising obtaining, via the device, a value of an environmental parameter in a vicinity of the subject at the time-of-day, and wherein applying the time-dependent relationship function to the obtained physiological parameter value comprises applying the time-dependent relationship function and an environmental-dependent relationship function to the obtained physiological parameter value via the processor to estimate the value of the physiological parameter at the selected metabolic state.

9. The method of claim 1, further comprising adjusting the time-dependent relationship function for one or more of the following prior to estimating the value of the physiological parameter at the selected metabolic state: calories consumed by the subject and blood oxygen level of the subject.

10. The method of claim 1, wherein the selected metabolic state includes one or more of the following: state of peak metabolism, state of lowered metabolism, state of rest.

11. The method of claim 1, wherein the device is configured to be attached to one or more of the following portions of a body of the subject: arm, wrist, leg, hand, foot, finger, toe, chest, head, hair, nose, waist, trunk, shoulder, neck, and ear.

12. The method of claim 1, wherein the device is configured to be embedded within clothing and other wearable objects.

13. An apparatus, comprising:
a housing configured to be attached to a subject;
a physiological sensor attached to the housing, wherein the physiological sensor detects and/or measures physiological information from the subject; and
at least one processor attached to the housing, wherein the at least one processor is configured to obtain from the physiological sensor a value of a physiological parameter of the subject at a time-of-day, and to estimate a value of the physiological parameter for the subject at a selected metabolic state by applying a time-dependent relationship function to the obtained physiological parameter value, wherein the selected metabolic state is different from a current metabolic state of the subject.

14. The apparatus of claim 13, wherein the processor is configured to:
obtain from the physiological sensor the value of the physiological parameter at the same time-of-day for multiple days;
determine an average value for the multiple obtained values; and
apply the time-dependent relationship function to the average value.

15. The apparatus of claim 13, wherein the processor is configured to:
determine if the subject is in a condition of heightened activity at the selected time-of-day by determining if a heart rate of the subject is at an elevated level; and
adjust the time-dependent relationship function for the elevated heart rate level of the subject prior to estimating the value of the physiological parameter at the selected metabolic state.

16. The apparatus of claim 13, wherein the processor is configured to:
obtain values of the physiological parameter of the subject at multiple times during at least one previous day;
generate a personalized time-dependent relationship function between a measured value of the physiological value and the estimated value of the physiological parameter at the selected metabolic state using the obtained values from the at least one previous day; and
estimating the value of the physiological parameter for the subject at the selected metabolic state by applying the personalized time-dependent relationship function to the obtained physiological parameter value.

17. The apparatus of claim 13, further comprising an environmental sensor attached to the housing that detects and/or measures environmental condition information in a vicinity of the subject, and wherein the processor is configured to obtain a value of an environmental parameter in a vicinity of the subject at the time-of-day from the environmental sensor, and to apply the time-dependent relationship function and an environmental-dependent relationship function to the obtained physiological parameter value to estimate the value of the physiological parameter at the selected metabolic state.

18. The apparatus of claim 13, wherein the processor is configured to adjust the time-dependent relationship function for one or more of the following prior to estimating the value of the physiological parameter at the selected metabolic state: calories consumed by the subject and blood oxygen level of the subject.

19. The apparatus of claim 13, wherein the processor is configured to adjust the time-dependent relationship function for blood oxygen level of the subject prior to estimating the value of the physiological parameter at the selected metabolic state.

20. The apparatus of claim 13, wherein the housing is configured to be attached to one or more of the following portions of the body of the subject: arm, wrist, leg, hand, foot, finger, toe, chest, head, hair, nose, waist, trunk, shoulder, neck, and ear.

21. The apparatus of claim 13, wherein the housing is configured to be embedded within clothing and other wearable objects.

22. The apparatus of claim 13, wherein the housing is configured to be embedded within the skin or within the body of the subject.

* * * * *